United States Patent
Sato et al.

(10) Patent No.: US 8,454,490 B2
(45) Date of Patent: Jun. 4, 2013

(54) BIOLOGICAL RHYTHM ADJUSTMENT METHOD, BIOLOGICAL RHYTHM ADJUSTMENT DEVICE, BIOLOGICAL RHYTHM ADJUSTMENT SYSTEM

(75) Inventors: Satoru Sato, Shiga (JP); Takayuki Ishiwata, Saitama (JP); Jun-ichiro Arai, Shiga (JP); Yukio Mori, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 1267 days.

(21) Appl. No.: 10/593,260

(22) PCT Filed: Mar. 18, 2005

(86) PCT No.: PCT/JP2005/004991
§ 371 (c)(1),
(2), (4) Date: Jul. 2, 2007

(87) PCT Pub. No.: WO2005/089849
PCT Pub. Date: Sep. 29, 2005

(65) Prior Publication Data
US 2007/0282159 A1    Dec. 6, 2007

(30) Foreign Application Priority Data
Mar. 19, 2004   (JP) .................................. 2004-080627

(51) Int. Cl.
*A61M 21/00*   (2006.01)
(52) U.S. Cl.
USPC ........................................................... 600/27
(58) Field of Classification Search
USPC ................. 600/26–28; 362/1–2; 601/15–22
See application file for complete search history.

(56) References Cited

U.S. PATENT DOCUMENTS

| | | | | |
|---|---|---|---|---|
| 4,600,723 A * | 7/1986 | Short et al. | ..................... | 514/416 |
| 5,006,985 A * | 4/1991 | Ehret et al. | ..................... | 705/1.1 |
| 5,047,006 A * | 9/1991 | Brandston et al. | .............. | 600/21 |
| 5,163,426 A * | 11/1992 | Czeisler et al. | ................. | 607/88 |
| 5,176,133 A | 1/1993 | Czeisler et al. | | |
| 5,395,301 A * | 3/1995 | Russek | ..................... | 601/41 |
| 5,658,222 A * | 8/1997 | Brown | ..................... | 482/52 |
| 6,164,787 A * | 12/2000 | Seki et al. | ..................... | 362/1 |

FOREIGN PATENT DOCUMENTS

| | | |
|---|---|---|
| JP | 05-3919 A | 1/1993 |
| JP | 07-136276 A | 5/1995 |
| JP | 09-114885 A | 5/1997 |
| JP | 09-306672 A | 11/1997 |
| JP | 2739725 B2 | 1/1998 |
| JP | 10-68787 A | 3/1998 |
| JP | 11-235385 A | 8/1999 |
| JP | 2987981 B2 | 10/1999 |
| JP | 2002-233592 A | 8/2002 |
| JP | 2003-10230 A | 1/2003 |
| WO | WO 2004/075714 A2 * | 9/2004 |

* cited by examiner

*Primary Examiner* — Charles A Marmor, II
*Assistant Examiner* — Catherine E Burk
(74) *Attorney, Agent, or Firm* — Global IP Counselors

(57) ABSTRACT

A biological rhythm is adjusted based on a time difference as well while individually dealing with moving subjects that move in accordance with moving schedules. In step S1, information including the moving schedule and biological information on the moving subject is input. In step S2, a sleeping schedule is set based on the information obtained in step S1. Step S2 is roughly divided into two steps. In the first step, parameters for setting the sleeping schedule are set based on the moving schedule and the biological information. In the next step, the sleeping schedule is set with the parameters obtained in the first step.

13 Claims, 6 Drawing Sheets

BIOLOGICAL RHYTHM ADJUSTMENT METHOD, BIOLOGICAL RHYTHM ADJUSTMENT DEVICE, BIOLOGICAL RHYTHM ADJUSTMENT SYSTEM

TECHNICAL FIELD

The present invention relates to techniques for adjusting a biological rhythm, which can contribute to a reduction in Jet Lag Syndrome (the so-called "jet lag"), for example.

BACKGROUND ART

Conventionally, methods of eliminating or reducing jet lag have been proposed. Such methods are illustrated in patent documents 1 to 4, for example. A patent document 5, for example, discloses a technique for controlling an ambient temperature in order to obtain a favorable sleeping state.

Patent Document 1: Japanese Patent Application Laid-Open No. 11-235385

Patent Document 2: Japanese Patent Application Laid-Open No. 7-136276

Patent Document 3: Japanese Patent Application Laid-Open No. 10-68787

Patent Document 4: Japanese Patent Application Laid-Open No. 9-114885

Patent Document 5: Japanese Patent No. 2987981

DISCLOSURE OF INVENTION

The techniques described in the patent documents 1 and 2 contribute to elimination of jet lag, but lack a viewpoint of considering the actual time difference with respect to the time and period to which the techniques are applied based on a time difference. The patent documents 3 and 4 propose processes based on a time difference, but lack a viewpoint of individually dealing with travelers.

In view of the above, the present invention has an object to adjust a biological rhythm based on a time difference as well while individually dealing with moving subjects that move in accordance with moving schedules.

A first aspect of a biological rhythm adjustment method according to the present invention includes (a) a step (S1) of inputting a moving schedule, and biological information on a subject that moves in accordance with the moving schedule, and (b) a step (S2) of setting a sleeping schedule for the subject based on the moving schedule and the biological information.

A second aspect of the biological rhythm adjustment method according to the present invention is the biological rhythm adjustment method according to the first aspect, wherein in the step (b), sleep of the subject is set to a first time/a second time correspondingly to an eastward route/a westward route of the moving schedule, respectively, the first time being shorter than the second time.

A third aspect of the biological rhythm adjustment method according to the present invention is the biological rhythm adjustment method according to the first or second aspect, wherein the step (b) includes at least one of (b-1) a step (S201; S302; S211) of introducing the subject to sleep by raising a body temperature of the subject, and (b-2) a step (S203, S304) of irradiating light on the subject after the subject is aroused.

For example, the step (b-1) includes a step of raising an ambient temperature of the subject, or a step of giving instructions encouraging to do exercise to the subject.

A fourth aspect of the biological rhythm adjustment method according to the present invention is the biological rhythm adjustment method according to the third aspect, wherein the step (b) further includes (b-3) a step (S204) of relaxing the subject after executing the steps (b-1) and (b-2) when the moving schedule is on an eastward route.

A fifth aspect of the biological rhythm adjustment method according to the present invention is the biological rhythm adjustment method according to the third aspect, wherein the step (b) further includes (b-4) a step (S301) of relaxing the subject prior to both of the steps (b-1) and (b-2) when the moving schedule is on a westward route.

For example, the step (S204, S301) of relaxing the subject includes a step of supplying music to the subject, or a step of giving instructions encouraging to do exercise to the subject, or a step of massaging the subject.

A sixth aspect of the biological rhythm adjustment method according to the present invention is the biological rhythm adjustment method according to any one of the first to fifth aspects, wherein the biological information includes a sleeping time and an arousal time of the subject, and the sleeping schedule is set based on the sleeping time and the arousal time as well in the step (b).

A first aspect of a biological rhythm adjustment device according to the present invention includes an information input unit (B1) inputting a moving schedule, and biological information on a subject that moves in accordance with the moving schedule, and a block (B21, B22) setting a sleeping schedule for the subject based on the moving schedule and the biological information.

Preferably, the block (B21, B22) includes a parameter-setting unit (B21) for setting the sleeping schedule based on the moving schedule and the biological information, and a sleep/arousal introducing unit (B22) setting the sleeping schedule with the parameters.

A second aspect of the biological rhythm adjustment device according to the present invention is the biological rhythm adjustment device according to the first aspect, wherein sleep of the subject is set to a first time/a second time correspondingly to an eastward route/a westward route of the moving schedule, respectively, the first time being shorter than the second time.

A third aspect of the biological rhythm adjustment device according to the present invention is the biological rhythm adjustment device according to the first or second aspect, wherein the sleep/arousal introducing unit (B22) includes a device (22f; 22g) raising a body temperature of the subject.

A fourth aspect of the biological rhythm adjustment device according to the present invention is the biological rhythm adjustment device according to any one of the first to third aspects, wherein the sleep/arousal introducing unit (B22) includes a device (22b, 22c) irradiating light on the subject.

For example, the device raising a body temperature of the subject includes an air conditioner (22f) raising an ambient temperature of the subject, or exercise equipment (22g), or preferably a device (22c, 22d) giving instructions encouraging to do exercise to the subject.

A fifth aspect of the biological rhythm adjustment device according to the present invention is the biological rhythm adjustment device according to any one of the first to fourth aspects, wherein the sleep/arousal introducing unit (B22) includes a device (22d, 22h, 22g) relaxing the subject.

For example, the device relaxing the subject includes a sound output device (22d), or exercise equipment (22g), or preferably a device (22c, 22d) giving instructions encouraging to do exercise to the subject. Alternatively, the device relaxing the subject may include a massager (22h).

A sixth aspect of the biological rhythm adjustment device according to the present invention is the biological rhythm adjustment device according to any one of the first to fifth aspects, wherein the biological information includes a sleeping time and an arousal time of the subject, and the sleeping schedule is set based on the sleeping time and the arousal time as well in the sleep/arousal introducing unit (B22).

A biological rhythm adjustment system according to the present invention includes the biological rhythm adjustment device according to the first to sixth aspects, wherein the sleep/arousal introducing unit (B22) is provided to an airplane seat in an aircraft, and the information input unit (B1) and the parameter-setting unit (B21) are provided separately from the airplane seat.

Preferably, the parameter-setting unit (B21) is provided in the crew's cabin in the aircraft.

Preferably, the information input unit (B1) is provided to a check-in counter for the aircraft.

A seventh aspect of the biological rhythm adjustment method according to the present invention includes a first step (S201; S211) of encouraging the onset of sleep before the onset of sleep, a second step (S212) of reducing an ambient temperature in a predetermined period of time following the onset of sleep, a third step (S212) of raising an ambient temperature in a prescribed period of time, from a point in time that goes back the prescribed period of time from a scheduled arousal time, and a fourth step (S203) of weakening drowsiness after arousal.

An eighth aspect of the biological rhythm adjustment method according to the present invention includes a first step (S301; S311) of interfering with the onset of sleep before the onset of sleep, a second step (S313) of reducing an ambient temperature in a predetermined period of time following the onset of sleep, a third step (S313) of raising the ambient temperature in a prescribed period of time, from a point in time that goes back the prescribed period of time from a scheduled arousal time, and a fourth step (S313) of interfering with arousal prior to the scheduled arousal time.

A ninth aspect of the biological rhythm adjustment method according to the present invention includes a first step (S201; S211) of encouraging the onset of sleep before the onset of sleep, a second step (S313) of reducing an ambient temperature in a predetermined period of time following the onset of sleep, a third step (S313) of raising an ambient temperature in a prescribed period of time, from a point in time that goes back the prescribed period of time from a scheduled arousal time after the onset of sleep, and a fourth step (S313) of interfering with arousal prior to the scheduled arousal time.

A tenth aspect of the biological rhythm adjustment method according to the present invention includes a first step (S301; S311) of interfering with the onset of sleep before the onset of sleep, a second step (S212) of reducing an ambient temperature in a predetermined period of time following the onset of sleep, a third step (S212) of raising an ambient temperature in a prescribed period of time, from a point in time that goes back the prescribed period of time from a scheduled arousal time, and a fourth step (S203) of weakening drowsiness after arousal.

Preferably in the seventh to tenth aspects, as an eleven aspect, after the ambient temperature reaches a lowest value in the second step, the ambient temperature is kept at the lowest value until the point in time of starting the third step.

According to the first aspect of the biological rhythm adjustment method of the present invention, a biological rhythm can be adjusted based on a time difference as well while individually dealing with moving subjects that move in accordance with moving schedules.

According to the second aspect of the biological rhythm adjustment method of the present invention, the biological rhythm is shortened and extended for an eastward direction and a westward direction, respectively.

According to the third aspect of the biological rhythm adjustment method of the present invention, sleep pressure of the moving subject is increased quickly in step (b-1). The biological rhythm after arousal is established in step (b-2).

According to the fourth aspect of the biological rhythm adjustment method of the present invention, arousal is further ensured.

According to the fifth aspect of the biological rhythm adjustment method of the present invention, sleep pressure is reduced.

According to the sixth aspect of the biological rhythm adjustment method of the present invention, sleeping hours are adjusted depending on the degree of pleasantness of sleep.

According to the first aspect of the biological rhythm adjustment device of the present invention, a biological rhythm can be adjusted based on a time difference as well while individually dealing with moving subjects that move in accordance with moving schedules.

According to the second aspect of the biological rhythm adjustment device of the present invention, the biological rhythm is shortened and extended for an eastward direction and a westward direction, respectively.

According to the third aspect of the biological rhythm adjustment device of the present invention, sleep pressure of the moving subject is increased quickly.

According to the fourth aspect of the biological rhythm adjustment device of the present invention, the biological rhythm after arousal is established.

According to the fifth aspect of the biological rhythm adjustment device of the present invention, arousal is ensured, and sleep pressure can be reduced.

According to the sixth aspect of the biological rhythm adjustment device of the present invention, sleeping hours are adjusted depending on the degree of pleasantness of sleep.

According to the biological rhythm adjustment system of the present invention, a biological rhythm can be adjusted while the moving subject is moving.

According to the seventh aspect of the biological rhythm adjustment method of the present invention, when advancing the onset of sleep time and arousal time, the reduction in ambient temperature after encouraging the onset of sleep results in a favorable sleeping state, and also allows a smooth introduction of arousal. Further, drowsiness after arousal, if it remains, can be weakened.

According to the eighth aspect of the biological rhythm adjustment method of the present invention, when delaying the onset of sleep time and arousal time, the reduction in ambient temperature after interfering with the onset of sleep results in a favorable sleeping state, and arousal is interfered with in a state where arousal is likely to occur during sleep, thereby maintaining the sleeping state until the arousal time.

According to the ninth aspect of the biological rhythm adjustment method of the present invention, long-time sleeping can be obtained.

According to the tenth aspect of the biological rhythm adjustment method of the present invention, short-time sleeping can be obtained.

According to the eleventh aspect of the biological rhythm adjustment method of the present invention, the favorable sleeping state is maintained since the ambient temperature is reduced down to the lowest value where the favorable sleeping state is obtained, and is kept at the lowest value.

These and other objects, features, aspects and advantages of the present invention will become more apparent from the following detailed description of the present invention when taken in conjunction with the accompanying drawings.

BEST MODE FOR CARRYING OUT THE INVENTION

Figure 1:
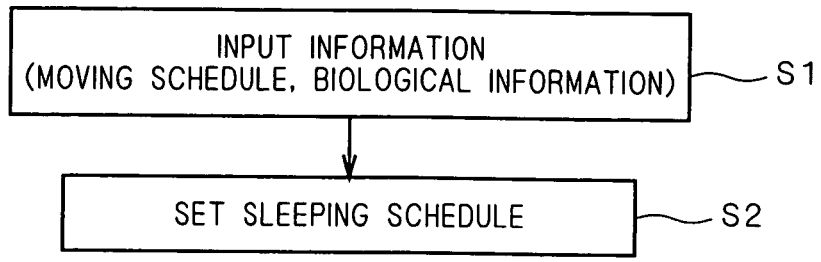
FIG. 1 is a flowchart showing a biological rhythm adjustment method according to the present invention.

FIG. 1 is a flowchart showing rough steps of a biological rhythm adjustment method according to the present invention. In the present invention, a sleeping schedule for a subject that moves in accordance with a moving schedule is set, and the so-called jet lag is reduced with the sleeping schedule. The moving schedule shall mean a travel schedule by aircraft, for example, and the subject that moves (hereafter called a "moving subject") shall mean a human being, for example. By way of example, sleep control in order to eliminate jet lag while moving by aircraft will be described below.

In step S1, information including the above moving schedule and biological information on the above moving subject is input. In step S2, a sleeping schedule is set based on the information obtained in step S1. Namely, a biological rhythm can be adjusted based on a time difference as well while individually dealing with the moving subjects that move in accordance with the moving schedules.

Figure 2:
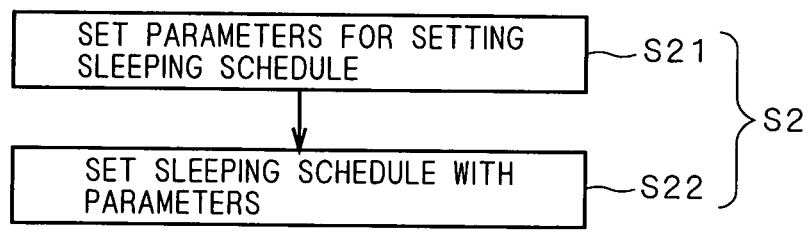
FIG. 2 is a flowchart showing the biological rhythm adjustment method according to the present invention.

FIG. 2 is a flowchart that divides step S2 roughly into steps S21 and S22. In step S21, parameters for setting the sleeping schedule are set based on the moving schedule and the biological information. In step S22, the sleeping schedule is set with the parameters obtained in step S21. The settings of the parameters and the sleeping schedule will be described later in detail.

Figure 3:
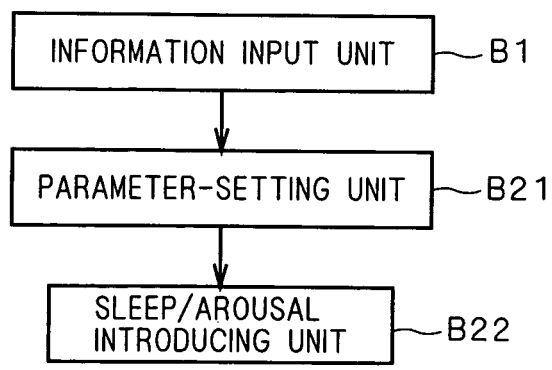
FIG. 3 shows a block diagram of the structure of a biological rhythm adjustment device according to the present invention.

FIG. 3 shows a block diagram of the structure of a biological rhythm adjustment device that executes the flowcharts shown in FIGS. 1 and 2. This device includes an information input unit B1 that executes step S1, a parameter-setting unit B21 that executes step S21, and a sleep/arousal introducing unit B22 that executes step S22. Namely, the parameter-setting unit B21 inputs information such as the moving schedule and the biological information, and supplies the information to the parameter-setting unit B21. The parameter-setting unit B21 generates parameters based on the above information. The sleep/arousal introducing unit B22 not only sets the sleeping schedule with those parameters, but executes various kinds of operations to encourage the moving subject to follow the sleeping schedule. The various kinds of operations will be described later in detail as well.

The information input unit B1, the parameter-setting unit B21, and the sleep/arousal introducing unit B22 can be provided together to an airplane seat, for example. Alternatively, the parameter-setting unit B21 and the sleep/arousal introducing unit B22 may be provided together to an airplane seat while providing the information input unit B1 apart from the airplane seat, with data being given and received by cable or by radio between them. For example, the information input unit B1 may be provided to the check-in counter. Still alternatively, only the sleep/arousal introducing unit B22 may be provided to an airplane seat while separating the information input unit B1 and the parameter-setting unit B21 from the airplane seat. For example, the information input unit B1 may be provided to the check-in counter and the parameter-setting unit B21 in the crew's cabin. The information input unit B1 may be connected to the parameter-setting unit B21 through the use of a communications network such as the Internet.

Figure 4:
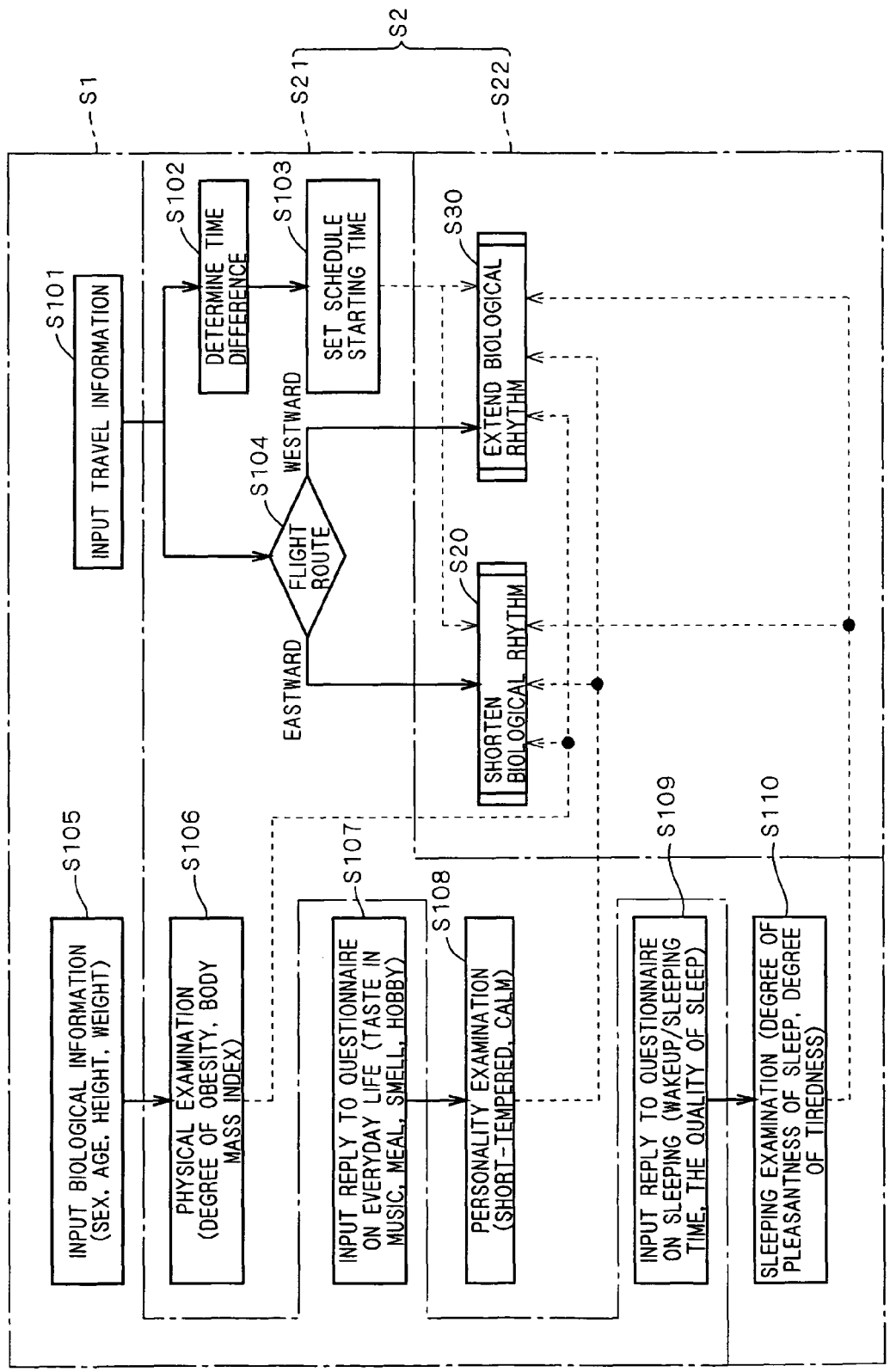
FIG. 4 is a flowchart showing the biological rhythm adjustment method according to the present invention.

FIG. 4 is a flowchart showing the details of the flowcharts shown in FIGS. 1 and 2. Step S1 includes steps S101, S105, S107 and S109, step S21 includes steps S102, S103, S104, S106, S108 and S110, and step S22 includes steps S20 and S30, respectively.

(i) Details of Step S1

In step S101, travel information is input. Specific examples of the travel information include a departure place, an arrival place, a travel route, a departure time, and an arrival time.

In step S105, biological information is input. Specific examples of the biological information include sex, age, height, and weight.

In step S107, a reply to a questionnaire on everyday life is input. Specific examples of the questionnaire on everyday life include a taste in music, meal and smell, and hobbies.

In step S109, a reply to a questionnaire on sleeping is input. Specific examples of the questionnaire on sleeping include bedtime (sleeping time), wakeup time (arousal time), and the quality of sleep. The quality of sleep includes "today's wakeup condition (whether you feel you have slept well)", and "whether you are satisfied with a recent sleeping state", for example.

(ii) Details of Step S21

In step S102, a time difference of the arrival place when viewed from the departure place is calculated and determined based on the travel information. In step S103, a starting time for each schedule in the sleeping schedule as described later is set based on the time difference.

In step S104, a direction of travel route is determined. Namely, whether eastward or westward is determined.

In step S106, a physical examination is carried out based on the biological information. More specifically, the degree of obesity and a body mass index of the moving subject are obtained, for example.

In step S108, a personality examination is carried out based on the reply to the questionnaire on everyday life. More specifically, an index is determined that indicates how short-tempered the moving subject is, for example.

In step S110, a sleeping examination is carried out based on the reply to the questionnaire on sleeping. More specifically, indexes of pleasantness of sleep and tiredness are determined, for example.

(iii) Details of Step S22

Steps S20 and S30 are selected to be executed when the travel route is eastward and westward, respectively. Step S20 sets a sleeping schedule for shortening a biological rhythm while step S30 sets a sleeping schedule for extending a biological rhythm, and both steps encourage the moving subject to follow their respective sleeping schedules.

The broken line arrows in FIG. 4 show that the parameters obtained in steps S103, S106, S108 and S110, namely, the time for starting each schedule in the sleeping schedule, the degree of obesity and the body mass index of the moving subject, the index indicative of how short-tempered the moving subject is, and the indexes of pleasantness of sleep and tiredness, set the details of the sleeping schedules of steps S20 and S30.

The direction of moving route is obtained in step S104, which too can be regarded as a parameter for setting the sleeping schedule. Yet the route direction, which is used for selecting and executing one of steps S20 and S30, is indicated by the solid line arrows in FIG. 4. From the viewpoint of step S22 including steps S20 and S30, however, it can be understood that the sleeping schedule is set with the parameters including the route direction as well. The same holds true for the relationship between the parameter-setting unit B21 and the sleep/arousal introducing unit B22.

In addition, the time for starting each schedule in the sleeping schedule (step S103) specifically servers as the reference for advancing or delaying the execution time of step S20 or S30, or for extending or shortening the time required for execution, for example.

Figure 5:
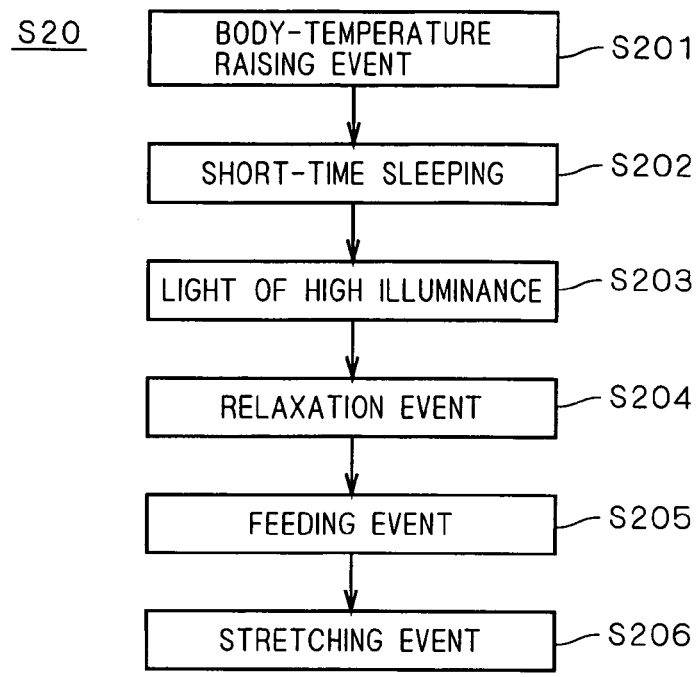
FIG. 5 is a flowchart showing the biological rhythm adjustment method according to the present invention.
Figure 6:
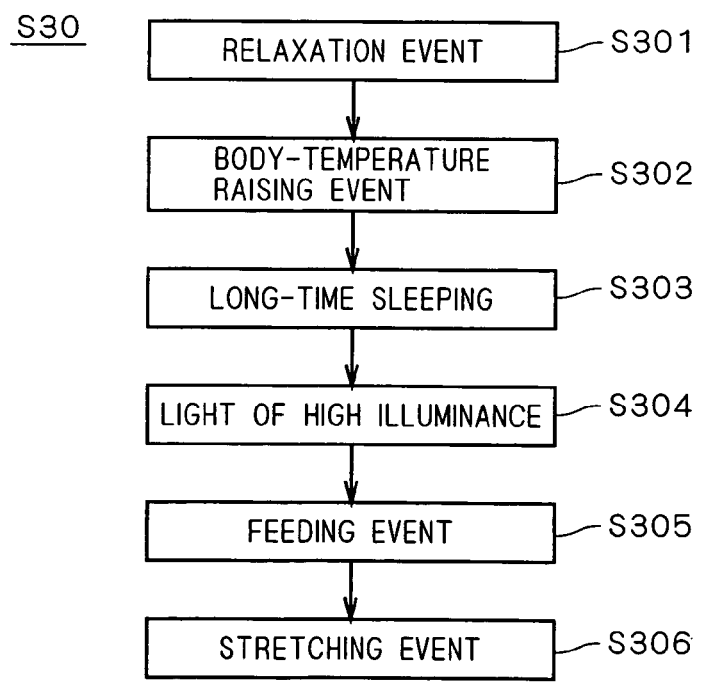
FIG. 6 is a flowchart showing the biological rhythm adjustment method according to the present invention.
Figure 7:
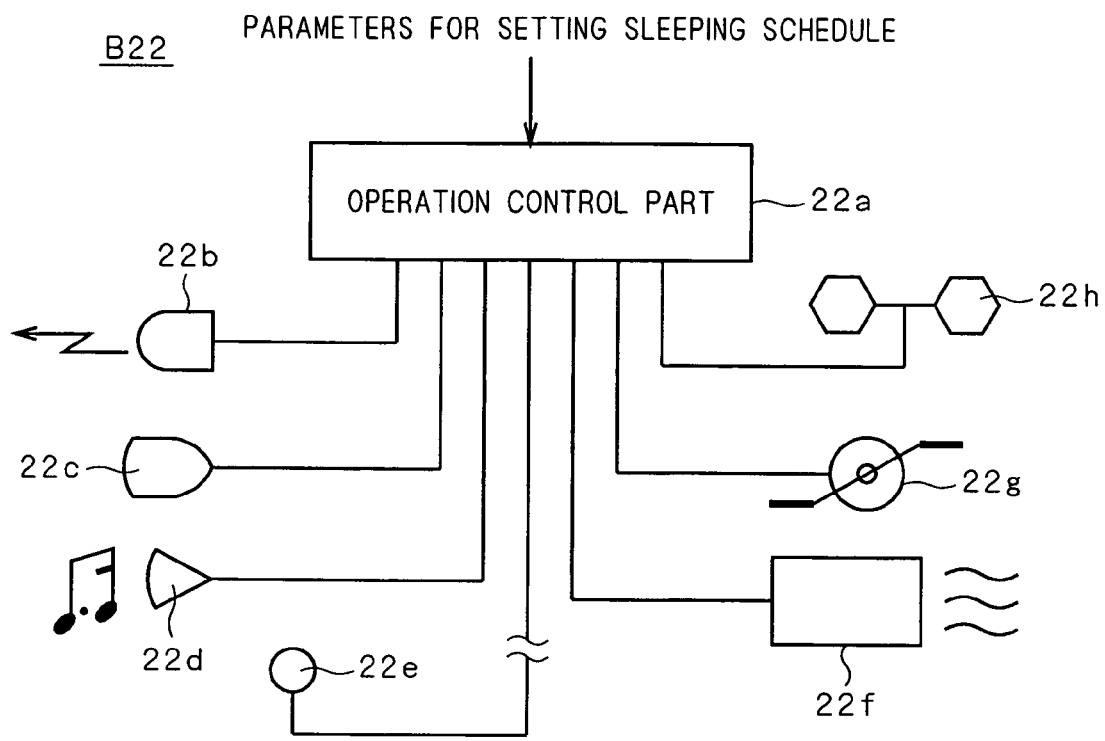
FIG. 7 shows a block diagram of the structure of the biological rhythm adjustment device according to the present invention.

FIGS. 5 and 6 are flowcharts showing the details of steps S20 and S30, respectively. FIG. 7 is a block diagram showing a detailed structure of the sleep/arousal introducing unit B22 that executes step S22.

The sleep/arousal introducing unit B22 includes devices 22b to 22h that execute various kinds of operations with the parameters for setting the sleeping schedule, and an operation control part 22a that controls the operations of these devices. By way of example, the device 22b is an irradiation device such as an LED, the device 22c is a display device such as a VDT, the device 22d is a sound output device such as a speaker or an earphone, the device 22e is an alarm such as a buzzer or a lamp, the device 22f is an air conditioner such as a warm air blower, the device 22g is exercise equipment the moving subject uses for exercise such as pedaling, and the device 22h is relaxation equipment such as a massager. The irradiation device 22b and the display device 22c may be combined together, or may be combined with a display installed in an airplane seat.

The operation control part 22a and the devices 22b to 22h can be provided together to an airplane seat. It is desirable, however, that the alarm 22e be arranged in the crew's cabin to provide notification to the crew, as described later. The alarm 22e may be combined with a cabin attendant call typically provided to an airplane seat, for example.

Further, the sound output device 22d may be combined with the functions of an earphone typically provided to an airplane seat.

(iv) Details of Step S20

As shown in FIG. 5, step S20 includes steps S201 to S206. In step S201, an event for raising a body temperature (hereafter and in the drawings called a "body-temperature raising event") is performed. Sleep pressure is thus increased quickly to shorten a biological rhythm.

As the body-temperature raising event, an ambient temperature of the moving subject is raised, or instructions encouraging to do exercise are given to the moving subject, for example. The ambient temperature of the moving subject is raised by the air conditioner 22f, for example. Alternatively, display encouraging exercise is given on the display device 22c. The instructions encouraging exercise may be announced by the sound output device 22d. The moving subject having received the instructions may use the exercise equipment 22g, for example, to do exercise. The body-temperature raising event may employ one or both of the two kinds of events described above, or still another method.

When raising the ambient temperature of the moving subject in step S201, while the ambient temperature is raised, the setting temperature is set low with an increase in the degree of obesity obtained in step S106, under the assumption of the higher the degree of obesity, the more sensitive to heat.

When encouraging the moving subject to do exercise in step S201, the amount of exercise is reduced with an increase in the degree of obesity obtained in step S106, under the assumption that the body temperature increases with a small amount of exercise. For example, the load applied to the moving subject from the exercise equipment 22g is reduced.

A period of execution of step S201 is reduced with an increase in index indicative of short-temperedness obtained in step S108. More specifically, the speed of raising the ambient temperature is increased, for example. Alternatively, the load applied to the moving subject from the exercise equipment 22g is increased to increase the amount of exercise per hour. Or the moving subject is subjected to anaerobic exercise. Conversely, a period of execution of step S201 may be extended with a decrease in index indicative of short-temperedness. For example, the amount of exercise per hour is reduced. Or the moving subject is subjected to aerobic exercise.

It is to be noted that the schedule starting time obtained in step S103 is also considered for a period of execution of step S201. This is because if a period of execution of step S201 is extended because of a low index indicative of short-temperedness, all the steps of step S20 will not be finished before landing when the schedule starting time is late. The same holds true for the other steps S202 to S206.

Processing then continues from step S201 to step S202. In step S202, a process for short-time sleeping is performed.

It is known that the body temperature regulation capability of a living body decreases during sleep, so that a body temperature can be easily controlled by a change in external temperature. Accordingly, the quality of sleep can be enhanced by increasing the depth of sleep. Temperature contributes not only to the falling asleep that determines the quality of sleep but to the depth of sleep.

More specifically, the ambient temperature is quickly reduced by the air conditioner 22f, for example. This quickly reduces the body temperature of the moving subject as well, thereby introducing the moving subject to a deep sleep state in a relatively short period of time. About four sleeping hours are set as standard.

The biological rhythm is advanced by adjusting the sleeping hours as described above, thereby eliminating jet lag.

The sleeping hours can be reduced with an increase in degree of pleasantness of sleep obtained in step S110 and a decrease in degree of tiredness. This is under the assumption that less sleep is required in such circumstances. Conversely, the sleeping hours are extended with a decrease in degree of pleasantness of sleep and an increase in degree of tiredness. Variation within plus or minus about one hour can be added to the four hours set as standard above.

The short-time sleeping in step S202 can be terminated by an arousal method with an alarm by the sound output device 22d, for example. Alternatively, the alarm 22e may notify the crew of the termination of sleeping hours, causing the crew to arouse the moving subject.

Processing then continues from step S202 to step S203. In step S203, light is irradiated on the moving subject. This establishes the biological rhythm after arousal. The light can be supplied to the moving subject from the irradiation device 22b or the display device 22c, for example. For the biological rhythm after arousal to be established, it is desirable that the light have a wavelength of not less than 5000 K in terms of color temperature, and illuminance of not less than 2500 lux to the moving subject. Light having illuminance of not less than 2500 lux and a color temperature of about 5000 K is supplied to the person. Light having illuminance of not less than 2500 lux makes the person strongly feel ambient brightness. Light having a color temperature of about 5000 K is blue-tinged and makes the person feel chillness through the sense of sight.

Processing then continues from step S203 to step S204. In step S204, an event for relaxation (hereafter and in the drawings called a "relaxation event") is performed. The arousal is thus further ensured. As the relaxation event, the moving subject is encouraged to take action to relax. For example, the moving subject is subjected to exercise, music listening, or a massage. When subjecting the moving subject to exercise, display encouraging exercise is given on the display device 22c or instructions are announced by the sound output device 22d as described above with respect to step S201. The moving subject having received the instructions may use the exercise equipment 22g, for example, to do exercise.

When subjecting the moving subject to music listening, display encouraging to listen to music is given on the display device 22c, or instructions are announced by the sound output device 22d, for example. The moving subject having received the instructions is then supplied with music from the sound output device 22d. The above instructions and music may be supplied in a reverse order. Alternatively, music may be supplied while omitting the instructions. It is desirable that the music be the so-called healing music, or sound effects and music that promote alpha waves. The degree of relaxation of the moving subject is thus increased.

Likewise, when subjecting the moving subject to a massage, display encouraging to get a massage is given on the display device 22c, or instructions are announced by the sound output device 22d. The moving subject having received the instructions is then massaged by the massager 22h. The above instructions and massage may be supplied in a reverse order. Alternatively, a massage may be supplied while omitting the instructions.

The higher the degree of obesity determined in step S106, the better for the moving subject to do exercise than get a massage. Also, the higher the degree of short-temperedness determined in step S108, the better it is to reduce a period of exercise. A lengthy exercise gives stress to the short-tempered moving subject, interfering with the effects of relaxation.

Processing then continues from step S204 to step S205. In step S205, an event for feeding the moving subject (hereafter and in the drawings called a "feeding event") S205 is performed. As the feeding event, the alarm 22e is used to notify the crew to supply the moving subject with a meal, for example.

It is desirable to supply a meal that is low in calorie, sugar and fat with an increase in the degree of obesity determined in step S106. The meal should further be low in protein in order to adjust the biological rhythm.

Processing then continues from step S205 to step S206. In step S206, a stretching event is performed that encourages the moving subject to stretch in preparation for landing. More specifically, display encouraging to stretch is given on the display device 22c, or instructions are announced by the sound output device 22d. The moving subject having received the instructions then stretches, to be prepared for activity at the arrival place.

(v) Details of Step S30

As shown in FIG. 6, step S30 includes steps S301 to S306. A relaxation event is performed in step S301 as in step S204, a body-temperature raising event is performed in step S302 as in step S201, light of high illuminance is irradiated in step S304 as in step S203, a feeding event is performed in step S305 as in step S205, and a stretching event is performed in step S306 as in step S206.

However, the relaxation event is performed after performing the body-temperature raising event and irradiation of high-illuminance light in step S20, whereas the relaxation event is performed prior to both of the body-temperature raising event and irradiation of high-illuminance light in step S30. This is to reduce sleep pressure to extend the biological rhythm.

The sleeping time is delayed in step S301, and then the body temperature is raised in step S302 to increase sleep pressure. After that, a process for long-time sleeping is performed in step S303. More specifically, the ambient temperature is gradually raised prior to a scheduled arousal time. This avoids arousal from a deep sleep depth while extending sleeping hours. About eight sleeping hours are set as standard, for example. The biological rhythm is delayed by adjusting the sleeping hours as described above, thereby eliminating jet lag.

Variation within plus or minus about one hour can be added to the eight hours depending on the degrees of pleasantness of sleep and tiredness obtained in step S110, as in step S202. As for arousal, an alarm by the sound output device 22d may be used, or the alarm 22e may notify the crew to arouse the moving subject, as described with respect to step S202.

(vi) Example as a System

As has been mentioned in describing FIG. 3, arrangement places of the information input unit B1, the parameter-setting unit B21, and the sleep/arousal introducing unit B22 can be changed in various ways.

Figure 8:
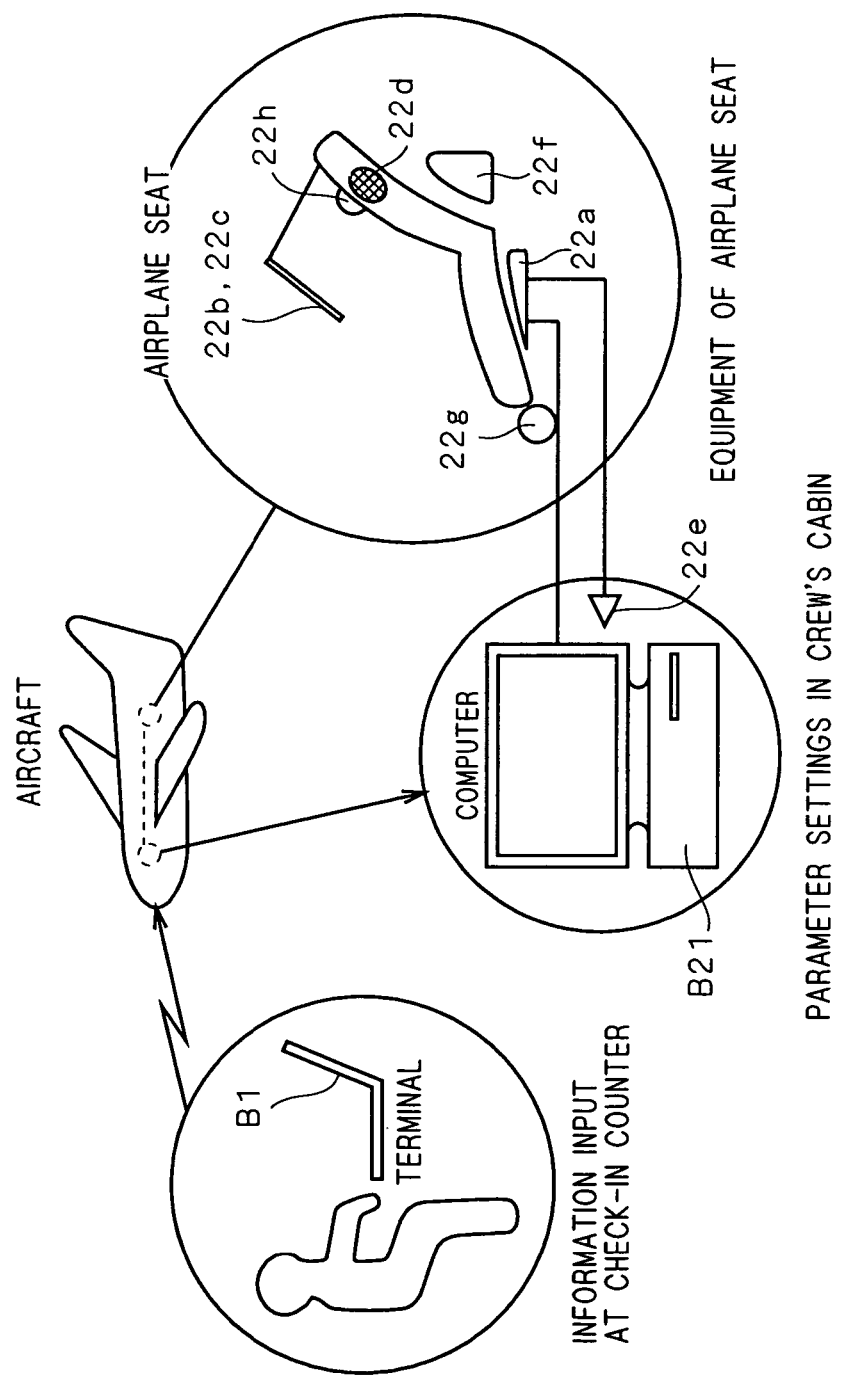
FIG. 8 illustrates a specific arrangement of the biological rhythm adjustment device according to the present invention.

FIG. 8 is a schematic view of an example where the biological rhythm adjustment device is specifically arranged as a system. In this exemplary configuration, all components of the sleep/arousal introducing unit B22 except the alarm 22e are provided to an airplane seat, the information input unit B1 is provided to the check-in counter, and the alarm 22e and the parameter-setting unit B21 are provided in the crew's cabin.

A terminal for example is provided as the information input unit B1 at the check-in counter, where a staff member inputs the travel information, the biological information, the reply to the questionnaire on everyday life, and the reply to the questionnaire on sleeping. The results are supplied by radio to a computer provided in the crew's cabin in the aircraft, to set the parameters for setting the sleeping schedule. Namely, this computer serves as the parameter-setting unit B21. Such provision of the parameter-setting unit B21 in the crew's cabin in the aircraft is desirable in that the parameters can be modified depending on a flight situation of the aircraft, and the conditions of a traveler which is the moving subject.

The operation control part 22a and the devices 22b to 22d and 22f to 22h are provided together to the airplane seat. The operation control part 22a is connected to the parameter-setting unit B21 and the alarm part 22e in the crew's cabin.

When arranging the biological rhythm adjustment device as a system, the parameter-setting unit B21 may of course be provided to the check-in counter, or to an airplane seat.

(vii) Other Variations

While it is preferable to perform both of the body-temperature raising event (S201, S302) and irradiation of high-illuminance light (S203, S304), one of them may alternatively be employed. This is because the former introduces sleep while the latter establishes a biological rhythm, thus producing different effects from each other.

The onset of sleep is encouraged by the following methods, for example. A first method of encouraging the onset of sleep is to raise an ambient temperature from a point in time that goes back a prescribed period of time from a scheduled onset of sleep time until the onset of sleep time, for example, to thereby raise the body temperature of a person. For example, a person feels moderate warmth and drowsy by raising the body temperature 0.2° C. from a point in time that goes back 30 to 60 minutes from a scheduled onset of sleep time until the onset of sleep time.

A second method of encouraging the onset of sleep is to supply a person with light having illuminance and a color temperature that have a calming effect from a point in time that goes back a prescribed period of time from a scheduled onset of sleep time until the onset of sleep time. For example, the person is supplied with light having illuminance of not more than 500 lux and a color temperature of not more than 1000 K from 60 minutes until 30 minutes prior to a scheduled onset of sleep time. Then, the person is supplied with light having illuminance of not more than 50 lux and a color temperature of not more than 1000 K from 30 minutes prior to the scheduled onset of sleep time until the onset of sleep time. Light having illuminance of not more than 500 lux makes the person feel ambient duskiness. Light having illuminance of not more than 50 lux makes the person feel ambient darkness. Light having a color temperature of not more than 1000 K is red-tinged and makes the person feel warmth through the sense of sight.

As step S211 that replaces the aforementioned steps S201 and S302, one of the first and second methods of encouraging the onset of sleep may be employed, or both methods may be parallelly employed.

Parallelly with the first and/or second method of encouraging the onset of sleep, the person may be supplied with a smell from the point in time that goes back a prescribed period of time from the scheduled onset of sleep time until the onset of sleep time. For example, the person is supplied with a smell of lavender, chamomile, or orange from 30 minutes prior to the scheduled onset of sleep time. Consequently, the person feels relaxed.

Alternatively, sounds transmitted to the person may be cut off from the point in time that goes back a prescribed period of time from the scheduled onset of sleep time until the onset of sleep time. For example, noise transmitted to the person trying to fall asleep is cut off from 30 minutes prior to the scheduled onset of sleep time. Consequently, the person can fall asleep in a quiet state.

Still alternatively, the person may be subjected to music listening from the point in time that goes back a prescribed period of time from the scheduled onset of sleep time until the onset of sleep time. For example, the person listens to music containing lots of alpha waves and music having a healing effect. Consequently, the person feels relaxed.

These methods can help encourage the onset of sleep. Namely, the execution of these methods simultaneously with the first and/or second method of encouraging the onset of sleep encourages the onset of sleep more effectively.

Figure 9:
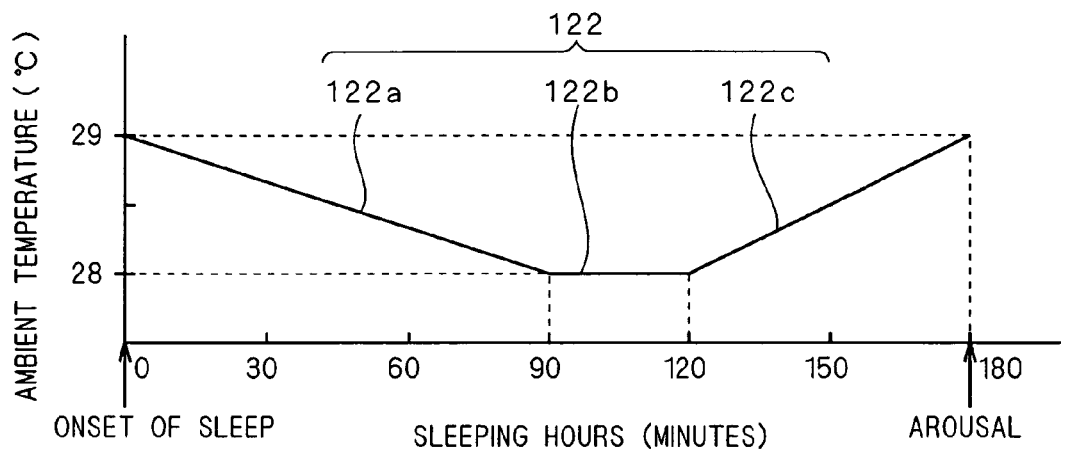
FIG. 9 shows a graph of a variation of the present invention.

The aforementioned step S202 may be replaced by the following step S212. FIG. 9 shows a graph indicating a change in ambient temperature with respect to sleeping hours by a solid line 122 in step S212. The solid line 122 includes sold lines 122a, 122b and 122c.

In step S212, the ambient temperature is first reduced, monotonously for example, in a predetermined period of time after the onset of sleep. Such change in ambient temperature is indicated by the solid line 122a in FIG. 9. The ambient temperature indicated by the solid line 122a is set to 29° C. at the onset of sleep. Then, about 90 minutes are employed as the predetermined period of time, during which the ambient temperature is monotonously reduced to about 28° C. The body temperature of the person decreases as the ambient temperature is reduced. Such method of controlling the ambient temperature is disclosed in the patent document 5, for example.

The body temperature is reduced in step S212 after executing step S201 or step S211 of encouraging the onset of sleep, thereby introducing the person to a favorable sleeping state.

The ambient temperature then reaches the lowest value, and is kept at the lowest value. Such change in ambient temperature is indicated by the solid line 122b in FIG. 9. The ambient temperature is kept at the lowest value of 28° C. for about 30 minutes.

Subsequently, the environment around the person before arousal is controlled. As the before-arousal control, at least one of a first method of before-arousal control of raising the ambient temperature, monotonously for example, in a prescribed period of time prior to a scheduled arousal time, and a second method of before-arousal control, is performed.

A change in ambient temperature controlled by the first method of before-arousal control is indicated by the solid line 122c in FIG. 9. About 60 minutes are employed as the prescribed period of time, during which the ambient temperature is monotonously raised from the lowest value of 28° C. to 29° C. The person is aroused after a lapse of the prescribed period of time. The body temperature of the person increases as the ambient temperature is raised. Such method of controlling the ambient temperature is also disclosed in the patent document 5, for example.

The contents of the first method of before-arousal control can be understood as raising the ambient temperature in a prescribed period of time, from a point in time that goes back the prescribed period of time from a scheduled arousal time.

In the second method of before-arousal control, the person is supplied with light having illuminance and a color temperature that have a stimulating effect from a point in time that goes back a prescribed period of time from a scheduled arousal time until an arousal time. For example, the person is supplied with light having illuminance of about 1000 lux and a color temperature of about 3000 K from 30 minutes prior to the scheduled arousal time. Light having illuminance of about 1000 lux makes the person feel ambient brightness. Light having a color temperature of about 3000 K is blue-tinged and makes the person feel chillness through the sense of sight.

Parallelly with the first and/or second method of before-arousal control, the person may be supplied with a smell from the point in time that goes back a prescribed period of time from the scheduled arousal time until the arousal time. For example, the person is supplied with a smell of peppermint, caffeine or basil from 30 minutes prior to the scheduled arousal time. Consequently, the person can feel refreshed, which helps encourage the arousal. Namely, the execution of this method parallelly with the first and/or second method of before-arousal control encourages the arousal more effectively.

When advancing the onset of sleep time and arousal time as described above, the reduction in ambient temperature after encouraging the onset of sleep results in a favorable sleeping state, and also allows a smooth introduction of arousal. Further, drowsiness after arousal, if it remains, can be weakened.

In addition, the favorable sleeping state is maintained since the ambient temperature is monotonously reduced down to the lowest value where the favorable sleeping state is obtained, and is kept at the lowest value. The maintenance of the ambient temperature at the lowest value may be omitted when the sleeping hours need to be further reduced.

The onset of sleep is interfered with by the following methods, for example. A first method of interfering with the onset of sleep is to keep an ambient temperature constant from a point in time that goes back a prescribed period of time from a scheduled onset of sleep time until the onset of sleep time, for example, to thereby keep the body temperature of a person constant. When the body temperature is kept constant, for example, the moderate warmth and the like that are felt when the body temperature increases is hard to generate, rendering it hard for the person to feel drowsy.

A second method of interfering with the onset of sleep is to supply a person with light having illuminance and a color temperature that have a stimulating effect from a point in time that goes back a prescribed period of time from a scheduled onset of sleep time until the onset of sleep time. For example, the person is supplied with light having illuminance of not less than 2500 lux and a color temperature of not less than 5000 K. Light having illuminance of not less than 2500 lux makes the person strongly feel ambient brightness. Light having a color temperature of not less than 5000 K is blue-tinged and makes the person feel chillness through the sense of sight.

In the first and second methods of interfering with the onset of sleep, the point in time that goes back a prescribed period of time from the scheduled onset of sleep time is set each time depending on how much the onset of sleep time is delayed.

As step S311 that replaces the aforementioned step S301, one of the first and second methods of interfering with the onset of sleep may be employed, or both methods may be simultaneously employed.

Parallelly with the first and/or second method of interfering with the onset of sleep, the person may be supplied with a smell from the point in time that goes back a prescribed period of time from the scheduled onset of sleep time until the onset of sleep time. For example, the person is supplied with a smell of peppermint, caffeine or basil. Consequently, the person feels refreshed.

Alternatively, the person may be subjected to music listening from the point in time that goes back a prescribed period of time from the scheduled onset of sleep time until the onset of sleep time. For example, the person listens to up-tempo music such as rock and pop music. Consequently, the person feels excited.

These methods help interfere with the onset of sleep. Namely, the execution of these methods parallelly with the first or second method interferes the onset of sleep more effectively.

In the method of supplying a smell and the method for music listening, the point in time that goes back a prescribed period of time from the scheduled onset of sleep time is set each time depending on how much the onset of sleep time is delayed. The settings may be associated with the aforementioned first and second methods, or may be made individually.

Figure 10:
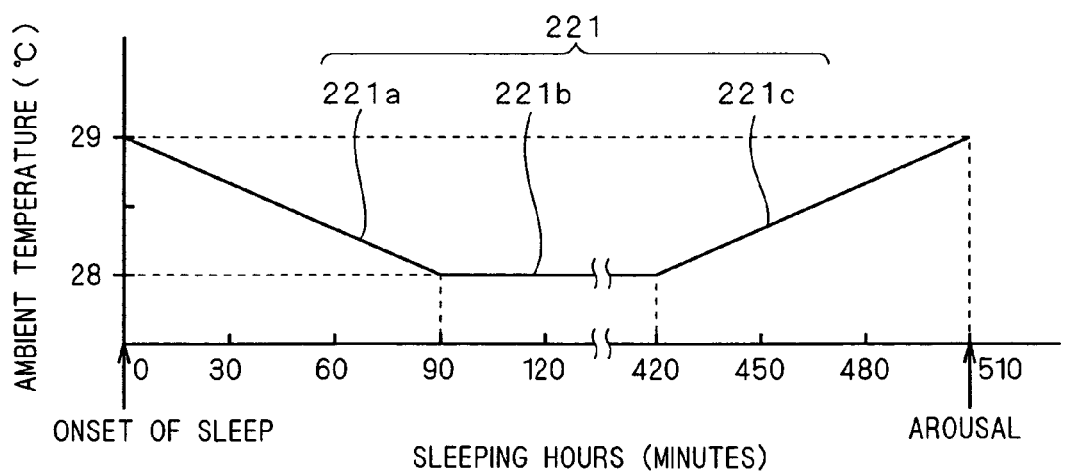
FIG. 10 shows a graph of a variation of the present invention.

The aforementioned step S303 may be replaced by the following step S313. FIG. 10 shows a graph indicating a change in ambient temperature with respect to sleeping hours by a solid line 221 in step S313. The solid line 221 includes sold lines 221a, 221b and 221c.

In step S313, the ambient temperature is first reduced, monotonously for example, in a predetermined period of time after the onset of sleep. Such change in ambient temperature is indicated by the solid line 221a in FIG. 10. The ambient temperature indicated by the solid line 221a is set to 29° C. at the onset of sleep. Then, about 90 minutes are employed as the predetermined period of time, during which the ambient temperature is monotonously reduced to about 28° C. The body temperature of the person decreases as the ambient temperature is reduced. Such method of controlling the ambient temperature is also disclosed in the patent document 4, for example.

The body temperature is reduced in step S313 after executing step S301 or step S311 of interfering with the onset of sleep, thereby introducing the person to a favorable sleeping state.

The ambient temperature then reaches the lowest value, and is kept at the lowest value. The change in ambient temperature controlled in step 23 is indicated by the solid line 221b in FIG. 4. The ambient temperature is kept at the lowest value of 28° C. for about 330 minutes.

Subsequently, the environment around the person before arousal is controlled. As control of the before-arousal control, at least one of a third method of before-arousal control of raising the ambient temperature, monotonously for example, in a prescribed period of time prior to a scheduled arousal time, and a fourth method of before-arousal control, is performed.

A change in ambient temperature controlled by the third method of before-arousal control is indicated by the solid line 221c in FIG. 10. About 90 minutes are employed as the prescribed period of time, during which the ambient temperature is monotonously raised from the lowest value of 28° C. to 29° C. The person is aroused after a lapse of the prescribed period of time. The body temperature of the person increases as the ambient temperature is raised.

The contents of the third method of before-arousal control can be understood as raising the ambient temperature in a prescribed period of time, from a point in time that goes back the prescribed period of time from a scheduled arousal time.

In the fourth method of before-arousal control, the person is supplied with light having illuminance and a color temperature that have a calming effect from a point in time that goes back a prescribed period of time from a scheduled arousal time until an arousal time. For example, the person is supplied with light having illuminance of about 500 lux and a color temperature of about 1000 K from 30 minutes prior to the scheduled arousal time. Light having illuminance of about 500 lux makes the person feel ambient duskiness. Light having a color temperature of about 1000 K is red-tinged and makes the person feel warmth through the sense of sight.

Parallelly with the third and/or fourth method of before-arousal control, the person may be supplied with a smell from the point in time that goes back a prescribed period of time from the scheduled arousal time until the arousal time. For example, the person is supplied with a smell of lavender, chamomile, or orange from 30 minutes prior to the scheduled arousal time. Consequently, the person feels relaxed and drowsy.

Alternatively, the person may be subjected to music listening from the point in time that goes back a prescribed period of time from the scheduled arousal time until the arousal time. For example, the person listens to music containing lots of alpha waves and music having a healing effect. Consequently, the person feels relaxed and drowsy.

These methods help interfere with the arousal. Namely, the execution of these methods simultaneously with the third and/or fourth method of before-arousal control interferes with the arousal more effectively.

When delaying the onset of sleep time and arousal time as described above, the reduction in ambient temperature after interfering with the onset of sleep results in a favorable sleeping state, and arousal is interfered with in a state where arousal is likely to occur during sleep, thereby maintaining the sleeping state until the arousal time.

In addition, the favorable sleeping state is maintained since the ambient temperature is monotonously reduced down to the lowest value where the favorable sleeping state is obtained, and is kept at the lowest value.

Moreover, when performing the short-time sleeping in step S212, the onset of sleep time may be delayed by interfering with the onset of sleep, and arousal may be encouraged to advance the arousal time. Alternatively, when performing the long-time sleeping in step S313, the onset of sleep time may be advanced by encouraging the onset of sleep, and arousal may be interfered with to delay the arousal time.

While the invention has been shown and described in detail, the foregoing description is in all aspects illustrative and not restrictive. It is therefore understood that numerous modifications and variations can be devised without departing from the scope of the invention.

The invention claimed is:

1. A biological rhythm adjustment device comprising:
   an information input unit receiving a moving schedule, and biological information on a subject that moves in accordance with said moving schedule; and
   a block setting a sleeping schedule for said subject based on said moving schedule and said biological information, the block including a parameter-setting unit for generating parameters based on said moving schedule and said biological information, and a sleep/arousal inducing unit setting said sleeping schedule with said parameters, said sleep/arousal inducing unit including a device raising a body temperature of said subject and a device relaxing said subject,
   the block inducing sleep of said subject for a first time period/a second time period correspondingly to an eastward route/a westward route of said moving schedule, respectively, said first time period being shorter than said second time period,
   the block reducing the body temperature of said subject to induce sleep of said subject for the eastward route, and the block reducing sleep pressure of said subject prior to inducing sleep of said subject for the westward route,
   the block reducing the ambient temperature around said subject to induce sleep of said subject for the eastward route,
   the block performing a relaxation event, then a body-temperature raising event to induce sleep and performing irradiation of high-illuminance light to induce waking of said subject for the westward route,
   the device relaxing said subject being set to initiate a relaxation event at a first time for the eastward route that is after a time at which the device raising the body temperature is set to initiate a body-temperature raising event, and
   the device relaxing said subject being set to initiate the relaxation event at a second time for the westward route that is before a time at which the device raising the body temperature is set to initiate the body-temperature raising event.

2. The biological rhythm adjustment device according to claim 1, wherein
   said sleep/arousal inducing unit includes a device irradiating light on said subject.

3. The biological rhythm adjustment device according to claim 1, wherein
   said device raising a body temperature of said subject includes an air conditioner raising an ambient temperature around said subject.

4. The biological rhythm adjustment device according to claim 1, wherein
   said device raising a body temperature of said subject includes exercise equipment.

5. The biological rhythm adjustment device according to claim 4, wherein
   said device raising a body temperature of said subject includes a device giving instructions encouraging to do exercise to said subject.

6. The biological rhythm adjustment device according to claim 1, wherein
   said device relaxing said subject includes a sound output device.

7. The biological rhythm adjustment device according to claim 1, wherein
   said device relaxing said subject includes exercise equipment.

8. The biological rhythm adjustment device according to claim 7, wherein
   said device relaxing said subject includes a device giving instructions encouraging to do exercise to said subject.

9. The biological rhythm adjustment device according to claim 1, wherein
   said device relaxing said subject includes a massager.

10. The biological rhythm adjustment device according to claim 1, wherein
    said biological information includes a sleeping time and an arousal time of said subject, and
    said sleeping schedule is set based on said sleeping time and said arousal time as well in said sleep/arousal inducing unit.

11. A biological rhythm adjustment system comprising:
    the biological rhythm adjustment device according to claim 1, wherein
    said sleep/arousal inducing unit is provided to an airplane seat in an aircraft,
    said information input unit and said parameter-setting unit are provided separately from said airplane seat.

12. The biological rhythm adjustment system according to claim 11, wherein
    said parameter-setting unit is provided in the crew's cabin in said aircraft.

13. The biological rhythm adjustment system according to claim 11, wherein
    said information input unit is provided to a check-in counter for said aircraft.

* * * * *